United States Patent [19]

Todd et al.

[11] Patent Number: 4,738,674
[45] Date of Patent: Apr. 19, 1988

[54] MOISTURE INDICATOR APPARATUS AND METHOD

[76] Inventors: Henry E. Todd, 72 Shadow La., Lakeland, Fla. 33803; Mildred Eidus, P.O. Box 260683, Tampa, Fla. 33685

[21] Appl. No.: 865,038

[22] Filed: May 19, 1986

Related U.S. Application Data

[63] Continuation of Ser. No. 797,753, Nov. 12, 1985, abandoned, which is a continuation of Ser. No. 496,836, May 23, 1983, abandoned.

[51] Int. Cl.$^4$ .............................................. A61F 13/16
[52] U.S. Cl. .................................................. 604/361
[58] Field of Search ................................. 604/358–361

[56] References Cited

U.S. PATENT DOCUMENTS

| | | | |
|---|---|---|---|
| 3,918,454 | 11/1975 | Korodi et al. | 604/361 |
| 3,952,746 | 4/1976 | Summers | 604/361 |
| 4,231,370 | 11/1980 | Mroz et al. | 604/361 |
| 4,507,121 | 3/1985 | Leung | 604/361 |

Primary Examiner—C. Fred Rosenbaum
Assistant Examiner—Sharon Rose
Attorney, Agent, or Firm—Dominik, Stein, Saccocio & Reese

[57] ABSTRACT

Moisture indicator strips of the capillary action type which provide a visual indication of wetness for diapers, hospital underpads, and the like, are located at a point removed from the actual point of wetness, such as at the edge of the diaper or surgical dressing. This invention further relates to a method for automatically and continuously incorporating a wetness indicator within the structure of the diaper or under pad during the manufacture thereof.

9 Claims, 2 Drawing Sheets

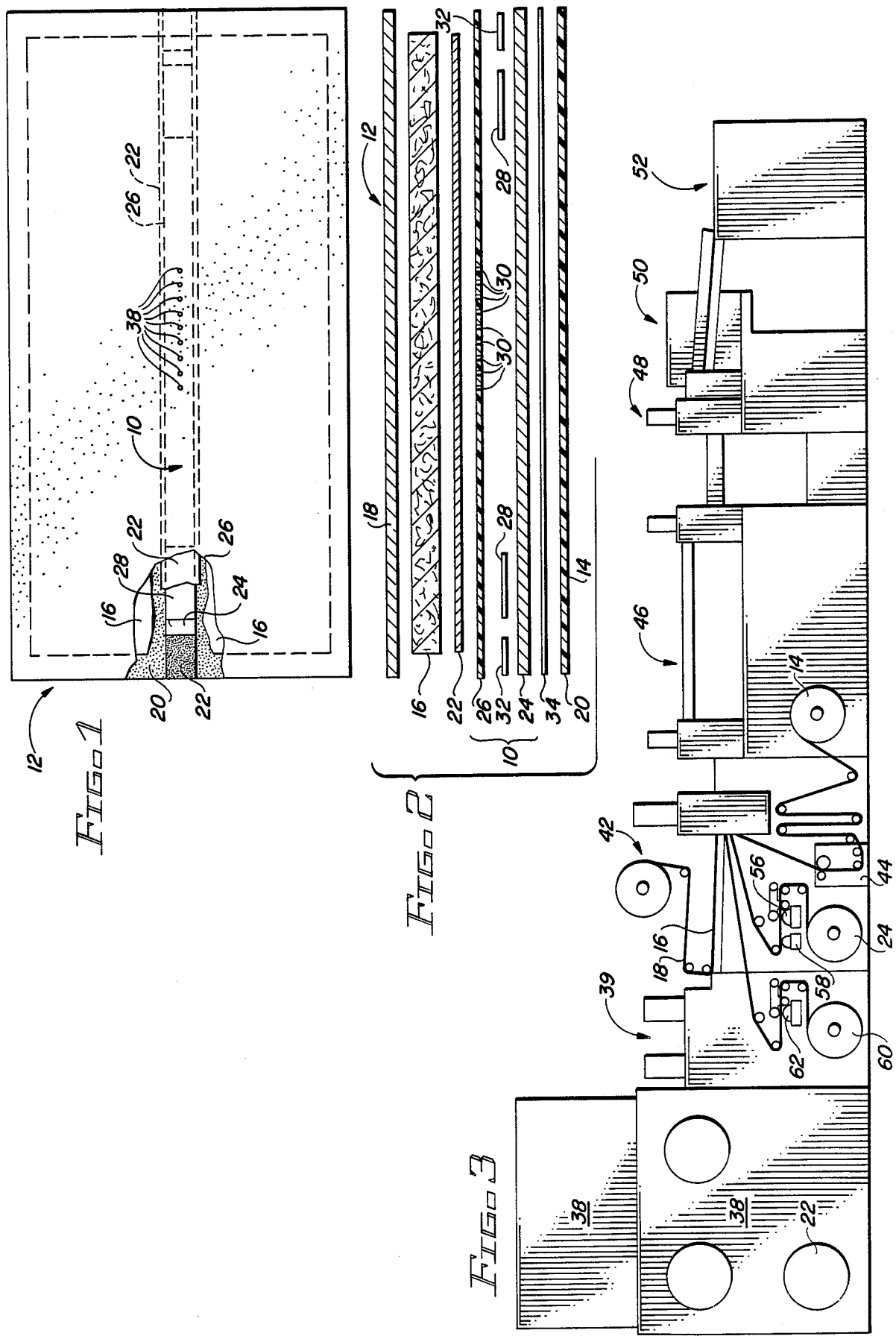

MOISTURE INDICATOR APPARATUS AND METHOD

This is a continuation of copending application Ser. No. 797,753 filed on Nov. 12, 1985 which is a continuation of Ser. No. 496,836 filed May 23, 1983.

BACKGROUND OF THE INVENTION

1. Field of the Invention

This invention relates to moisture indicator strips for diapers, hospital underpads, and the like. More particularly, this invention relates to moisture indicators of the capillary action type which provides a visual indication of wetness at a point removed from the actual point of wetness, such as at the edge of the diaper or surgical dressing. Further, this invention relates to a method for automatically and continuously incorporating a wetness indicator within the structure of the diaper or underpad during the manufacture thereof.

2. Description of Prior Art

Presently there exists many types of wetness indicators for use in conjunction with diapers, surgical dressings, hospital underpads, and the like. Basically, these types of wetness indicators can be classified into three broad categories: those which consist of imprinting a moisture indicating pattern on one of the plies of the diaper or underpad; those which consist of a discrete moisture indicating strip or layer which is incorporated between the layers of the diapers or underpad; and, those which consist of a discrete indicating strip which may be fastened to the interior of the diaper or underpad immediately prior to use.

U.S. Pat. Nos. 3,675,654 and 4,022,211 teach the general concept of imprinting a moisture indicating design onto the translucent moisture impervious outer covering of the diaper or underpad. One obvious advantage to this concept is the fact that the imprinting can be performed continuously during the manufacture of the diaper or underpad. Unfortunately, one major disadvantage to this concept is the fact that the only portion of the imprint which changes color is that which is in direct contact with the moisture. Obviously, such limited indication of wetness is highly undesirable in that the actual area of wetness itself may be obstructed from view. For example, in the case of diapers, it is well-known that only the crotch area of the wearer becomes wet during urination and that, therefore, the color change reflected by the imprint would be limited to the crotch area. If the wearer is dressed in a pair of shorts or trousers, this visual indication of wetness will, indeed, be of little significance in that such would be obstructed from view by the wearer or his/her attendant.

The second broad category of wetness indicators are those which consist of a discrete moisture indicating layer or strip which is incorporated within the plies of the diaper, underpad, or the like. U.S. Pat. Nos. 2,249,867, 3,759,261, 3,918,433, 3,918,454, 3,952,746, 4,192,311, and 4,231,370, and French Patent No. 1,355,018 teach the general concept of the second broad category of moisture indicators. Specifically, each of these patents teach the concept of incorporating a discrete ply(ies) or strip(s) into the diaper. In some embodiments, a single ply or strip is incorporated within the layers of the diaper which is impregnated or treated with various chemical compositions that experience a change in color upon becoming wet by urine or other moisture. In other embodiments, two or more plies are used wherein a first ply is colored or includes other visible indication means and wherein a second ply functions to obscure the view of the first colored ply until the second ply becomes translucent or transparent so as to no longer obscure or hide the first colored ply, thereby allowing the first colored ply to be viewed by the wearer or his/her attendant.

These patents of the second broad category suffer the same disadvantages of the first broad category of wetness indicators in that each of them only provides an indication of wetness at the precise zone of actual wetness, thereby being, in most applications, of marginal value. Further, these discrete moisture indicators cannot be automatically incorporated into the diaper during the manufacture thereof without unduly increasing the cost of manufacture of the diaper. Accordingly, these discrete moisture indicators of the second broad category have not been accepted by the industry.

Finally, the third broad category of moisture indicators consists of a capillary-type moisture indicating strip as taught by U.S. Pat. No. 3,731,685. Basically, this capillary-type moisture indicating strip consists of a strip having one end designed to be exposed to and receive the moisture and the other end impregnated with a chemical which changes color when wetted by the moisture. The strip comprises a wicking material which is capable of supporting capillary action such that moisture is transported from its moisture receiving end to its chemically impregnated end which experiences a change in color when exposed to such moisture. The strip itself is specially designed to be used in conjunction with diapers, surgical dressings, hospital underpads, sanitary napkins, and the like. Experience has shown that this type of capillary action strip works remarkably well to provide an indication of wetness at a point remote from the actual point of wetness, thereby overcoming the common, major disadvantage of those types of wetness indicators of the two broad categories outlined above. However, like the discrete moisture indicators of the second category above, this capillary-type moisture indicator of third category is also a discrete component which, in its present form, also unduly increases the cost of the diaper, underpad, etc. during the manufacture thereof. As a result, this capillary-type moisture indicator has achieved commercial success only by selling it as a separate article of manufacture. In this manner, the consumer has the opportunity to utilize a capillary-type moisture indicating strip in conjunction with any type of diaper, underpad, surgical dressing, et cetera. The disclosure of each of the eleven above identified patents are hereby incorporated by reference herein.

Therefore, it is an object of this invention to provide an apparatus and method which overcomes the aforementioned inadequacies of the prior art devices and provides an improvement which is a significant contribution to the advancement of the moisture indicating art.

Another object of this invention is to provide a capillary-type moisture indicating strip which provides a visual indication of wetness at a point removed from the actual point of wetness to conveniently indicate a condition of wetness when the point of wetness is obscured from view.

Another object of this invention is to provide a capillary-type moisture indicating strip particularly suited for diapers and hospital underpads and the like.

Another object of this invention is to provide a method of incorporating a capillary-type moisture indicating strip into the diaper or underpad during the manufacture thereof without interrupting or reducing the speed of the production of such diaper or underpad.

Another object of this invention is to provide a capillary-type moisture indicating strip which provides a visual indication of wetness at a point removed from the actual point of wetness while precluding leakage of the moisture at the point of visual indication.

Another object of this invention is to provide a method for indicating a condition of moisture at a point removed from the actual point of moisture while preventing such moisture from leaking onto the surrounding areas adjacent to the point of viewing.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing this invention, this invention comprises a capillary-type moisture indicating strip for diapers, hospital underpads, sanitary napkins, surgical dressings and the like. For the purposes of the summary, the detailed description of the preferred embodiment, the drawings and the claims, reference of the invention will be made with respect only to diapers. However, it shall be understood that the invention may alternatively be used in conjunction with all similar articles such as hospital underpads, surgical dressings, sanitary napkins, et cetera which function to absorb a fluid and which are manufactured in a manner similar to the manufacture of diapers.

Basically, the apparatus comprises a capillary-type moisture indicating strip having a strip of wicking material capable of supporting capillary action. Preferably, the wicking material is encapsulated along its length on one side by the moisture imprevious outer ply of the diaper and on the other side by a moisture imprevious strip having a width greater than the wicking strip. A plurality of holes is provided at least at the center portion of the moisture imprevious strip so as to allow moisture to pass therethrough to be absorbed by the wicking strip. The ends of the wicking strip are sealed by a blocking substance such as an adhesive absorbed by the wick so as to prevent the moisture from leaking from the ends of the wicking material. Finally, an amount of moisture indicating substance is applied at one or more points along the wicking material, preferably adjacent to one or both ends of the wicking material. The moisture indicating substance is designed to change color as the moisture in drawn by capillary action along the length of the wick and comes into contact with the moisture indicating substance.

The method of the invention basically comprises incorporating the above described improved moisture indicating strip into the diaper during the manufacture thereof. More specifically, during the manufacture of the diaper, the wicking strip is continuously fed into contact with the non-opaque outer covering of the diaper, preferably at the longitudinal center region thereof. State-of-the-art applicators are registered with the flow of the outer ply of the diaper to apply the blocking substance and the moisture indicating substance to the wicking strip so as to coincide with the beginning and the end of the diaper. Further simultaneously, the moisture imprevious strip is fed into contact with the other side of the wicking strip. A hole-making device is registered with the flow of the outer ply of the diaper so as to punch holes in the moisture imprevious coating to be located approximately at the center of the diaper. Alternatively, the moisture imprevious strip may be preapplied directly to the other side of the wicking strip, with the combination being then fed into contact with the outer ply of the diaper. Also alternatively, the plurality of holes and/or the moisture indicating substance may be prepunched/preapplied in/to the moisture imprevious strip/wicking strip prior to assembly. Finally, the absorbent, fiberized mat and the non-woven material, commonly used in most diapers, are fed into position against the outer surface of the moisture imprevious strip.

From the foregoing, it should be appreciated that the novel capillary-type moisture indicating strip of the invention can be continuously manufactured with the manufacture of the diaper by the unique method summarized above. This overcomes all of those disadvantages experienced by the prior art moisture indicators as outlined in the descripotion of the prior art above. Specifically, the unique method of the invention does not interfere with nor decrease the speed of production of the diapers. Further, the necessary spindles on which are stored the wicking strip and the moisture imprevious strip and the blocking substance applicator, the moisture indicator substance applicator, and the the hole puncher can be incorporated within existing diaper manufacturing machines without requiring any substantial alteration of the diaper manufacturing machine. Finally, the incorporation of the capillary-type wetness indicator of the invention and the diaper provides a visual indication of wetness at a point remote from the actual point of wetness; namely, at the front and rear edges of the diaper. This provides a visual indication of wetness at the upper edge of the diaper which, of course, is most convenient to check by the wearer or his/her attendant.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a plan view of a diaper having the capillarytype moisture indicating strip of the invention incorporated therein.

FIG. 2 is an exploded, cross-sectional view of FIG. 1 along lines 2—2, illustrating the various plies of the diaper and illustrating the capillary-type moisture indicator of the invention; and, FIG. 3 is a schematic representation of the method of the invention illustrating the manner in which the capillarytype mositure indicating strip of the invention is automatically and continuously incorporated within the diaper during the manufacture thereof.

Similar reference characters refer to similar parts throughout the several views of the drawings.

DETAILED DESCRIPTION OF THE PREFERRED EMBODIMENT

FIGS. 1 and 2 illustrate the capillary-type moisture indicator 10 of the invention incorporated within a diaper 12. Conventionally, most diapers 12 comprise a translucent or transparent outer ply 14 manufactured from a moisture impervious material such as polythene. The diaper 12 further includes a fiberized mat 16 manufactured from an absorbent material such as fluffed pulp wadding. Alternatively, in some diapers 12, the fiberized mat 16 actually comprises a plurality of piles of wadding which are sandwiched together. Finally, the inner ply of the diaper 12 comprises a non-woven material 18 which permits fluid to pass therethrough to be absorbed by the fiberized mat 16 and to provide a comfortable surface adjacent to the wearer of the diaper 12. Typically, an adhesive 20 is applied to the interior surface of the outer ply 14 of the moisture impervious plastic. This adhesive 20 functions to retain the fiberized mat 16 in position against the outer ply 14 and, with the fiberized mat 16 being of a size appreciably smaller than the outer ply 14, the adhesive 20 seals the outer peripheral edges of the outer ply 14 and the inner ply 18 together to encapsulate the fiberized mat 16 therebetween. Further, in most manufacturing machines which use the fluffed pulp wadding as a fiberized mat 16, the fluffed pulp wadding is conveyed during manufacture by a tissue carrier 22.

The capillary-type moisture indicator 10 of the invention comprises a wicking strip 24 capable of supporting capillary action. The wicking strip 24 is preferably positioned longitudinally along the center of the diaper 12 such that the center of the wicking strip 24 is located at the approximate center of the diaper 12. This assures that the center of the wicking strip 24 will be proximate to the crotch area of the wearer of the diaper 12. The wicking strip 24 is positioned immediately adjacent to the outer ply 14 of moisture impervious plastic and is adhered into position by means of adhesive 20. Another strip, herein referred to as a moisture impervious strip 26, is then positioned on the other side of the wicking strip 24. Preferably, but not necessarily required, the moisture impervious strip 26 may include a width appreciably greater than the width of the wicking strip 24 such that the longitudinal edges of the moisture impervious strip 26 are also adhered to the outer ply 14 by means of adhesive 20. This has the effect of encapsulating the wicking strip 24 along its entire longitudinal length.

A moisture indicating substance 28 is applied to a portion of the wicking strip 24, preferably at least at both ends thereof. The particular chemical composition of the moisture indicating substance 28 is selected so as to change color upon contact with moisture such as urine. Many suitable chemical compositions are disclosed in the above identified patents, the disclosures of which were incorporated herein by reference. Further, by way of example, the chemical composition may comprise a non-irritating vegetable dye which has been approved for human ingestion.

A plurality of holes 30 are formed in the impervious strip, preferably within the approximate center of the moisture impervious strip 26 to allow moisture such as urine to be absorbed by the wicking strip 24 and, due to capillary action, travel along the length of the wicking strip 22 to contact the moisture indicating substance 28. Alternatively, a plurality of slots or other aperatures may be formed in the approximate center of the moisture impervious strip 26 to allow passage of the fluid therethrough to the wicking strip 24.

Preferably, a capillary blocking substance 32 such as an adhesive is applied to the terminal ends of the wicking strip 24 to block the capillary action of the fluid flowing along the length of the wicking strip 24 from flowing out of the terminal ends of the wicking strip 24. This assures that the none of the fluid, such as urine, will leak from the diaper 12 and contaminate the wearer. Further, as noted earlier in a preferred embodiment, the encapsulation of the wicking strip 24 by the moisture impervious strip 26 and the outer ply 14 of moisture impervious plastic precludes leakage of the fluid along the length of the wicking strip 24, except in the location of urination; namely, the center area of the diaper 12 at which the holes 30 are located.

Depending on the drying characteristics of the adhesive 20, it may be desireable or preferable to apply a partially impervious coating 34 to the outer side of the wicking strip 24 during the manufacture of the wicking strip 24 and prior to incorporation within the diaper 12. Such a coating 34 will prevent the adhesive 20 from being absorbed by the wicking strip 24 in any manner that would adversely affect the capillary action of the wicking strip 24.

The method of the invention is schematically illustrated in FIG. 3. Summarizing, diapers 12 are typically manufactured by first fiberizing wood pulp in a fiberizer 38 to produce the fluffed pulp. The fluffed pulp is conveyed by a tissue carrier 22 for transport down-line. The fluffed pulp, now known as a fiberized mat 16, is then cut to size by a mat cut-off apparatus 39. The non-woven material 18 is typically stored on a spindle and fed onto the interior (upper) surface of the fiberized mat 16 as generally shown by numeral 42. Similarly, a spindle of the outer ply 14 is fed from below the fiberized mat 16 at a position down line from the now-combined non-woven material 18 and fiberized mat 16. A glue-printer 44 is provided to apply the adhesive 20 to the outer ply 14 immediately prior to its mating relationship with the fiberized mat 16. The entire mated combination is then moved into a drying zone generally represented by the numeral 46. Finally, the diaper 12 is cut to size by a cutting apparatus 48, cross-folded by a cross-folder 50 and stored within a bin 52.

The method of the invention schematically represents storing a supply of the wicking strip 24 on a spindle below the fiberized mat 16. The moisture indicating substance 28 is applied to the wicking strip 24 by means of an applicator 56. Similarly, the capillary blocking substance 32 is applied to the wicking strip 24 by a like applicator 58. Of course, the applicators 56 and 58 are registered with the flow of the fiberized mat 16 so as to properly apply the moisture indicating substance 28 and the capillary blocking substance 32 to the wicking strip 24 to coincide with the edges of the diaper 12.

A supply of the moisture impervious strip 26 is similarly stored on a spindle 60 at a position below the fiberized mat 16. The moisture impervious strip 26 is fed off of the spindle 60 and passes through a hole puncher apparatus 62. The hole puncher apparatus 62 is preferably designed to punch a plurality of holes 30 in the moisture impervious strip 26 and, if the holes are preferred to be positioned in the approximate center of the diaper 12, registered with the flow of the fiberized mat 16.

The wicking strip applicator 56 is located upstream from the flow of the non-woven material 18 and the moisture impervious strip applicator 58 is then located upstream of the wicking strip applicator 56.

Without departing from the scope of the method of the invention, the wicking strip 24 may be manufactured and assembled with the moisture impervious strip 26 and then stored on a roll such that both the wicking strip 24 and the moisture impervious strip 26 are fed together into proper position against the outer ply 14. Similarly, the moisture indicating substance 28 may be preapplied to a portion, or the entire length, of the wicking strip 24 during manufacture thereof. Finally, the moisture impervious strip 26 may be prepunched prior to being fed into the diaper machine and/or prepunched prior to being preassembled with the wicking strip 24. Obviously, it is desirable to prepunch the moisture impervious strip 26, preapply the moisture indicating substance 28 to the wicking strip 26 and then combine the same such that the entire assembly is fed into position against the outer ply 14 immediately after the capillary blocking substance 32 is applied to the wicking strip 26.

It should be appreciated that the method described above can be incorporated in practically any type of diaper manufacturing machine without any substantial alteration to the same. Further, it should also be appreciated that the method of the invention does not interfere with nor decrease the speed of operation of the diaper machine. Accordingly, this novel method of the invention permits the moisture indicator 10 of the invention to be economically incorporated within existing diapers 12 without any increase in the cost of the diaper 12 except for the costs of materials and equipment associated with the moisture indicator 10 itself.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described,
What is claimed is:

1. A moisture indicator for use in conjunction with a garment such as a diaper, hospital underpad or the like, having an outer ply of non-opaque, moisture impervious material and an inner ply of moisture absorbing material, comprising in combination:
   a wicking strip capable of supporting capillary action along its length, said wicking strip extending from one end of the garment to the other end of the garment;
   moisture indicating substance which visually indicates contact with moisture;
   said moisture indicating substance positioned at a portion of said wicking strip;
   means for affixing said wicking strip to the inside surface of the outer ply of the garment such that moisture contacting said wicking strip flows by capillary action along the length of said wicking strip to contact said moisture indicating substance to visually indicate the presence of moisture; and
   a moisture impervious strip positioned at least partially along the length of said wicking strip to prevent leaking of the moisture from said wicking strip at that portion of the wicking strip beyond the actual point where moisture is present.

2. The moisture indicator as set forth in claim 1, further including a capillary blocking substance positioned at the ends of said wicking strip to prevent the capillary flow of the moisture from leaking from the ends of said wicking strip.

3. The moisture indicator as set forth in claim 1, wherein said moisture impervious strip extends along the entire length of said wicking strip and includes a plurality of apertures at the anticipated point of moisture so as to encapsulate said wicking strip while allowing the moisture to be absorbed by said wicking strip for capillary flow along the length of said wicking strip.

4. The moisture indicator as set forth in claim 3 wherein said means for affixing said wicking strip to the outer ply of the garment comprises an adhesive.

5. The moisture indicator as set forth in claim 4, further including a coating of at least partially impervious coating applied to the outer surface of said wicking strip in contact with said adhesive such that said adhesive is precluded from adversely affecting the capillary flow characteristic of said wicking strip.

6. The moisture indicator as set forth in claim 5, wherein the garment comprises a diaper and wherein said wicking strip extends longitudinally along the center of the diaper with said aperture being located proximate to the crotch area of the diaper.

7. The moisture indicator as set forth in claim 6, wherein the garment comprises an underpad and wherein said wicking strip is located along the longitudinal length of the underpad such that said apertures are located proximate to the center of the underpad.

8. A method for producing a garment such as a diaper, hospital underpad or the like having a moisture indicator positioned between an outer ply of non-opaque, moisture impervious material and an inner ply of moisture absorbing material, the method comprising the steps of:
   providing a continuous supply of the moisture absorbing material;
   providing a continuous supply of an apertured moisture impervious strip, the apertures being located proximate to the area of anticipated wetness;
   providing a continuous supply of a wicking strip;
   applying a moisture indicating substance to the wicking strip;

applying a capillary blocking substance to the wicking strip;
providing a continuous supply of the moisture impervious material;
applying an adhesive to the moisture impervious material; and
thereafter applying the wicking material to the moisture impervious material in the area of anticipated wetness, applying the apertured moisture impervious strip over the wicking strip, applying the moisture absorbent material over the apertured moisture impervious strip and thereafter supplying combined layers to a cutting apparatus for cutting the combination into predefined garment sizes such that the capillary blocking substance is registered at the ends of the garment and the moisture indicating substance is registered near the ends.

9. A moisture indicating garment such as a diaper, hospital underpad or the like having an outer ply of non-opaque, moisture impervious material and an inner ply of moisture absorbing material and a moisture indicator therebetween, said moisture indicator comprising:
a wicking strip capable of supporting capillary action along its length, said wicking strip extending from one end of the garment to the other end of the garment;
moisture indicating substance located only near the ends of the wicking strip;
means for affixing the wicking strip to the inside surface of the outer ply such that moisture contacting said wicking strip flows by capillary action along the length of said wicking strip to the moisture indicating substance such that the presence of moisture is visually indicated; and
a moisture impervious strip between the wicking strip and the absorbent material said impervious strip overlying the wicking strip except in the region of anticipated wetness.

* * * * *